US00PP30430P2

(12) United States Plant Patent
Pineau

(10) Patent No.: US PP30,430 P2
(45) Date of Patent: Apr. 23, 2019

(54) ***ABELIA* PLANT NAMED 'MINACARA1'**

(50) Latin Name: *Abelia grandiflora*
Varietal Denomination: MINACARA1

(71) Applicant: Patrick Pineau, Saint Mathurin sur Loire (FR)

(72) Inventor: Patrick Pineau, Saint Mathurin sur Loire (FR)

(73) Assignee: Hortival Diffusion SAS (FR)

( * ) Notice: Subject to any disclaimer, the term of this patent is extended or adjusted under 35 U.S.C. 154(b) by 0 days.

(21) Appl. No.: 15/732,603

(22) Filed: Nov. 30, 2017

(51) Int. Cl.
*A01H 5/00* (2018.01)

(52) U.S. Cl.
USPC ..... Plt./226
CPC ..... *A01H 5/00* (2013.01)

(58) Field of Classification Search
USPC ..... Plt./226, 263.1
CPC ..... A01H 5/00
See application file for complete search history.

*Primary Examiner* — Kent L Bell
(74) *Attorney, Agent, or Firm* — Cassandra Bright

(57) ABSTRACT

A new and distinct *Abelia* cultivar named 'MINACARA1' is disclosed, characterized by a compact and semi-erect plant form. Plants have three distinctive foliage seasons during the year. Foliage color is orange in Spring, yellow and green-orange in Summer, and red to maroon in Autumn. Flowers are of medium size, colored light lavender and white. The new variety is an *Abelia*, normally produced as an outdoor garden or container plant.

4 Drawing Sheets

Latin name of the genus and species: *Abelia grandiflora.*
Variety denomination: 'MINACARA1'.

BACKGROUND OF THE INVENTION

The new *Abelia* cultivar is a product of a planned breeding program conducted by the inventor in La Menitre, France. The objective of the breeding program was to produce new *Abelia grandiflora* varieties with colorful foliage and compact habits for container production. The crossing resulting in this new variety was made during July of 2010.

The seed parent is *Abelia grandiflora* 'MINEDWARD' U.S. Plant Pat. No. 22,360, the pollen parent is *Abelia grandiflora* 'Francis Masson', unpatented. The new variety was identified as a potentially interesting selection during July of 2012. Selection was made at a research nursery in La Menitre, France.

Asexual reproduction of the new cultivar 'MINACARA1' was first performed in August of 2012 at a commercial nursery in La Menitre, France. Vegetative soft wood cuttings used. Subsequent propagation has shown that the unique features of this cultivar are stable and reproduced true to type in successive generations.

SUMMARY OF THE INVENTION

The cultivar 'MINACARA1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MINACARA1' These characteristics in combination distinguish 'MINACARA1' as a new and distinct *Abelia* cultivar:

1. Compacted, semi-erect plant form.
2. Three colors of foliage each year; orange in Spring, yellow and green-orange in Summer, and red to maroon in Autumn.
3. Medium sized flower colored white and light lavender.

PARENT COMPARISON

Plants of the new cultivar 'MINACARA1' are similar to plants of the seed parent variety in most horticultural characteristics, however, plants of the new cultivar 'MINACARA1' differ in the following;

1. The new variety has foliage colored orange in Spring, yellow to green-orange in Summer and red to maroon in Autumn. The seed parent foliage is red and green in Spring and green in Summer and Autumn.
2. Foliage of the new variety is larger in both width and length than foliage of the seed parent.
3. Plants of the new variety are more vigorous than plants of the seed parent.
4. Plants of the new variety are more upright than the more rounded seed parent.
5. Flower color of the new variety is white and light lavender, flower color of the seed parent is single color, all light lavender.
6. Sepal color of the new variety is green and red with white, sepal color of the seed parent is darker, brown-red.

Plants of the new cultivar 'MINACARA1' are similar to plants of the pollen parent variety in most horticultural characteristics, however, plants of the new cultivar 'MINACARA1' differ in the following;

1. The new variety has foliage colored orange in Spring, yellow to green-orange in Summer and red to maroon in Autumn. The pollen parent has foliage colored light yellow-orange in Spring, light yellow in Summer, and green-orange in Autumn.

COMMERCIAL COMPARISON

Plants of the new cultivar 'MINACARA1' can be compared to the variety *Abelia* 'Rika1' U.S. Plant Pat. No. 20,568. These varieties are similar in most horticultural characteristics however, 'MINACARA1' differs in the following:

1. The new variety has 3 seasons of different foliage color. This comparator has 2 seasons of foliage color.
2. Fall color of the new variety is red to maroon, Fall color of 'Rika1' is bronze-orange.
3. Flowers of the new variety are white and light lavender, flowers of 'Rika1' are white.

BRIEF DESCRIPTION OF THE PHOTOGRAPHS

The accompanying photograph in FIG. 1 illustrates in full color typical Spring foliage of 'MINACARA1' grown outdoors, at approximately 2 years old.

Figure 1:
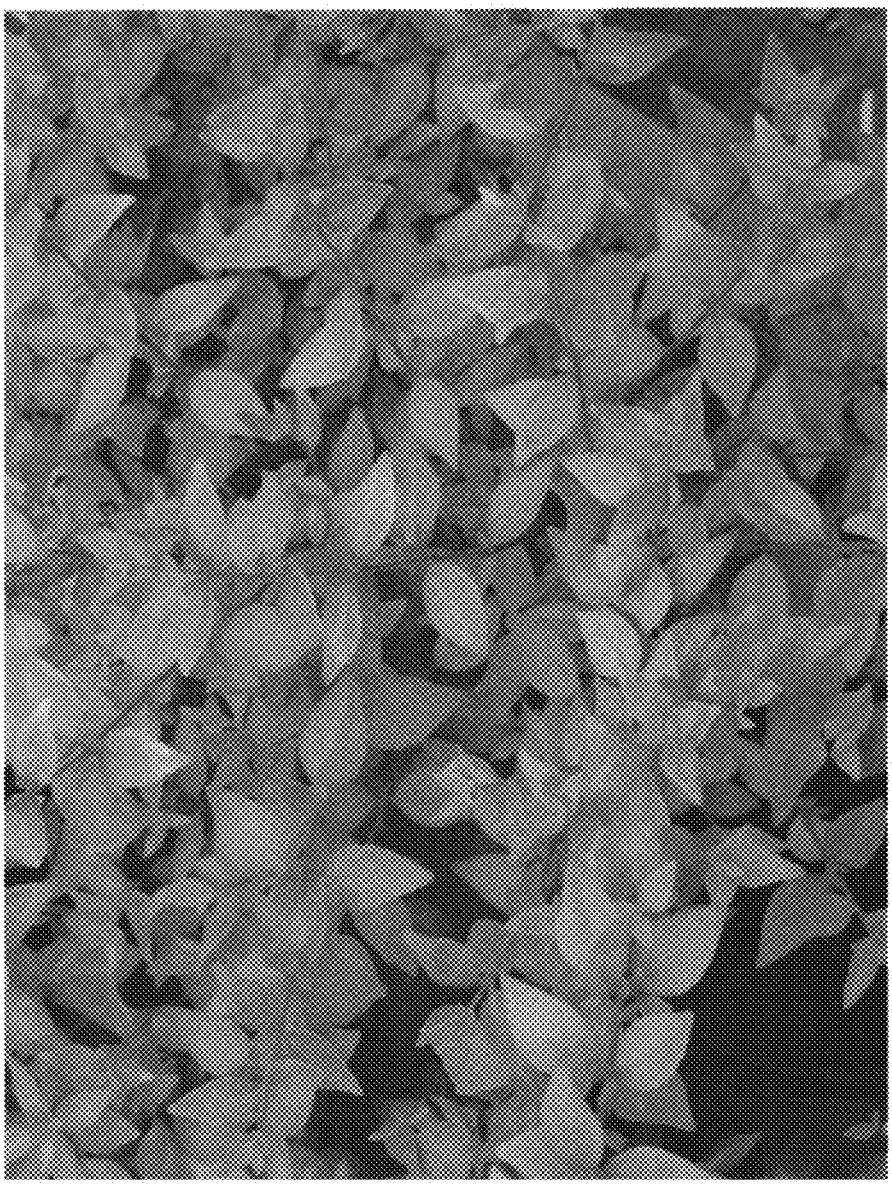
Figure 2:
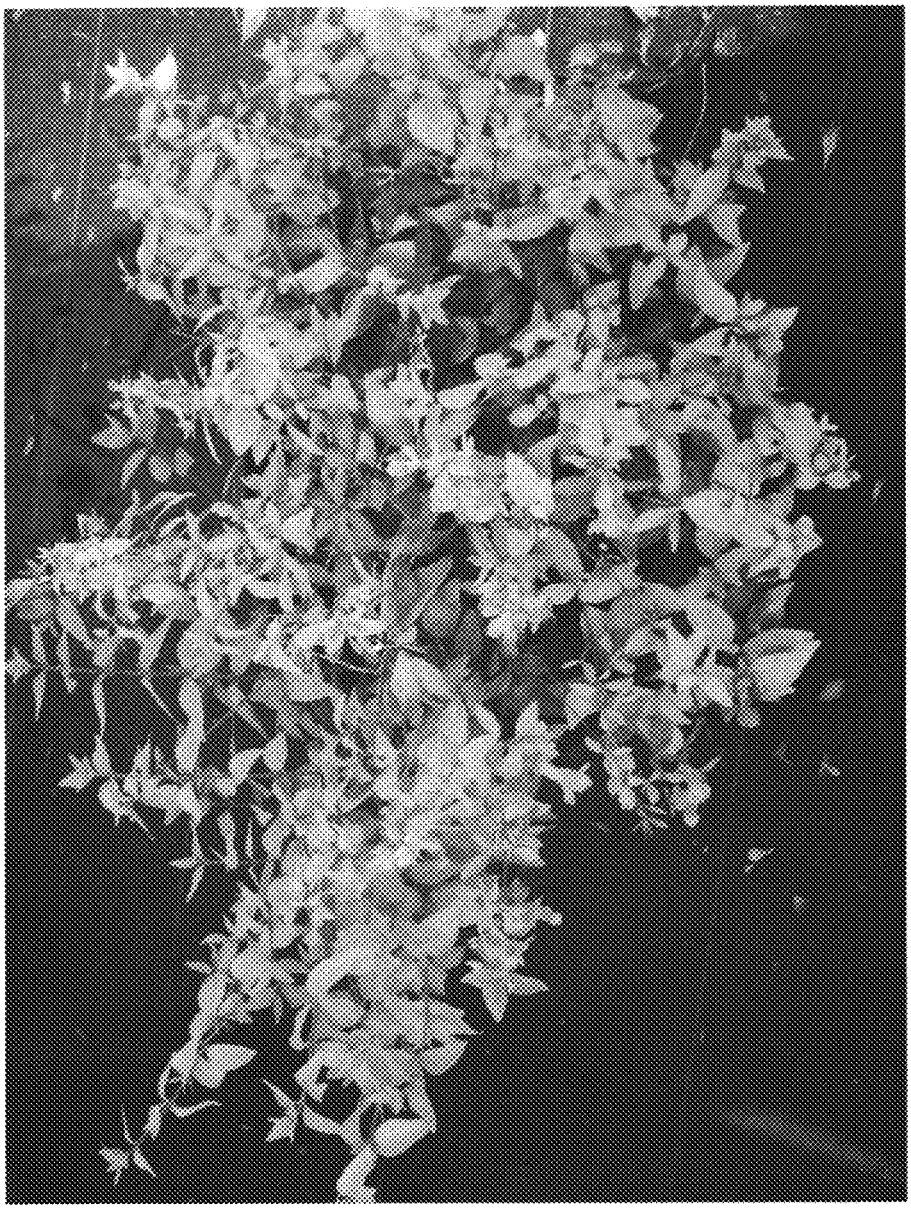
FIG. 2 illustrates a plant of 'MINACARA1' during the Summer, with yellow-green foliage, closeup view of the foliage, including new Spring growth.
Figure 3:
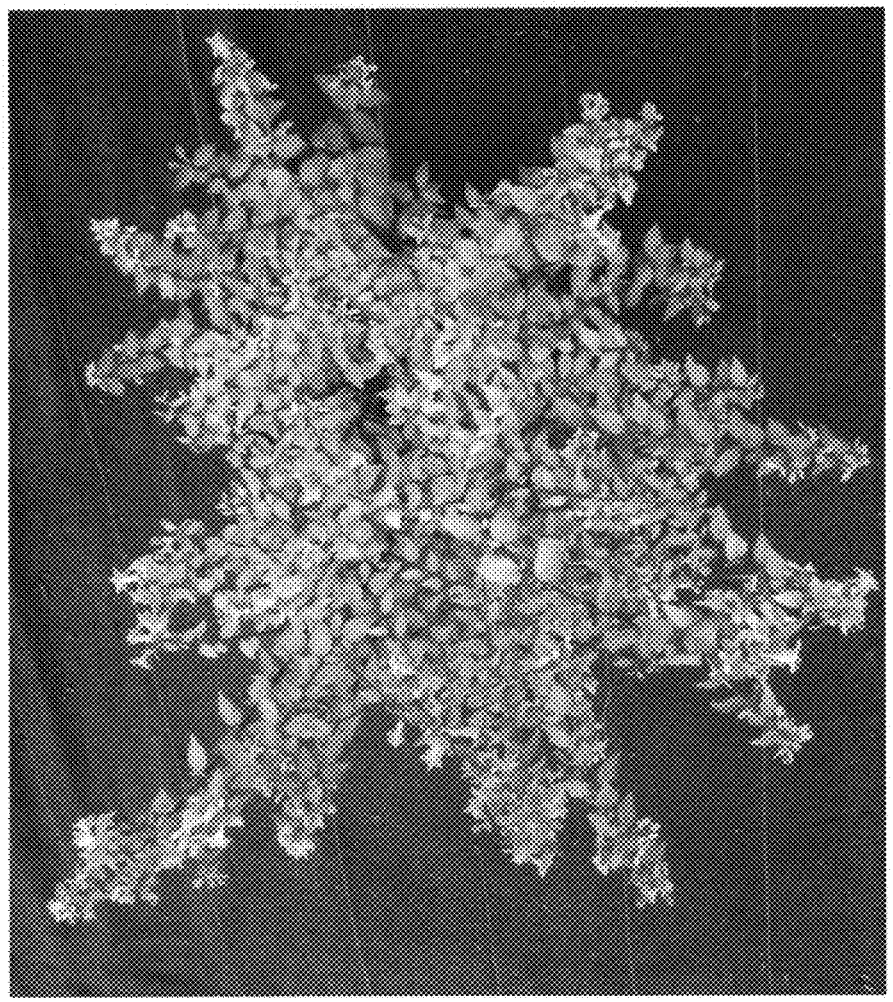
FIG. 3 illustrates in full color a plant of 'MINACARA1' during late Summer, turning bronze red to maroon for Autumn.
Figure 4:
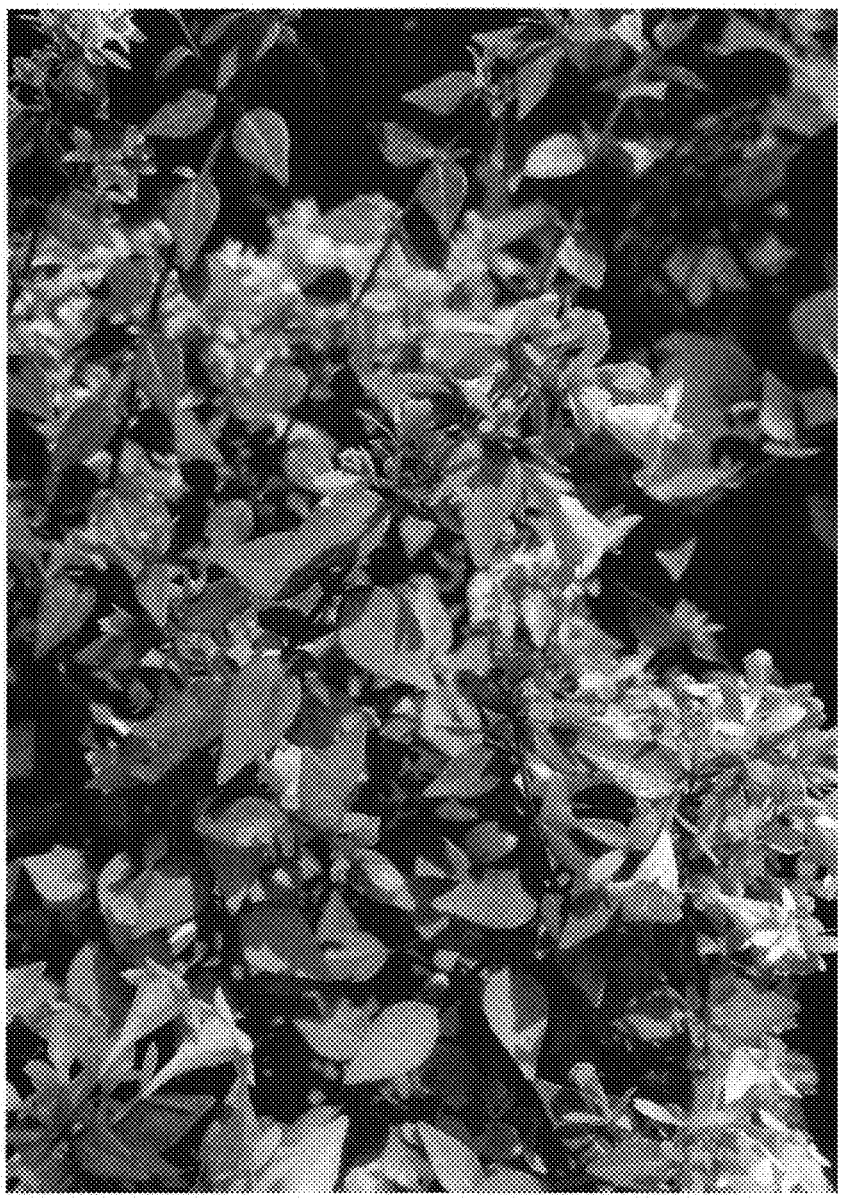
FIG. 4 illustrates flowers and foliage during late Summer to early Autumn.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, 6$^{th}$ edition, except where general terms of ordinary dictionary significance are used. The following observations and measurements describe 'MINACARA1' plants grown in a polyhouse in Grand Haven, Mich. Measurements were taken during May. The plants were about 2 years old in 5 gallon containers. The growing temperature ranged from approximately 18° C. to 27° C. during the day and 5° C. to 10° C. at night. Measurements and numerical values represent averages of typical plant types.

Botanical classification: *Abelia grandiflora* 'MINACARA1'.

PROPAGATION

Time to initiate roots: 1 to 2 months at approximately 18 to 27° C.

Root description: Fibrous, thin root thickness. Some fleshy roots, also thin. Tan and white in color, not effectively measured with a color chart.

Time to produce a rooted young plant: About 40 days at approximately 18 to 27° C.

PLANT

Plant type: Perennial flowering shrub.

Age of plant described: Approximately 2 to 3 years old.

Growth habit: Compact, semi-erect.

Pot size of plant described: 3 gallon pot.

Overall plant shape: Globular upright.

Height: 62 cm.

Plant spread: 86 cm.

Plant vigor: Strong.

Branching characteristics: Basal and lateral branching. Pinching required.

Length of primary lateral branches: Average 25 cm.

Diameter of lateral branches: 6 mm.

Quantity of lateral branches: Average 50 to 70.

Stem:

*Stem shape.*—Round.

*Stem strength.*—Strong.

*Color.*—Young: Near Greyed-Red 179A. Mature: Near Greyed-Green 195B and Greyed-Orange 174A.

*Texture.*—Pubescent.

*Angle of attachment.*—15 to 60 degrees from center of plant.

Internode length: 3 cm on average.

FOLIAGE

Leaf:

*Arrangement.*—Whorled and opposite. Single.

*Leaf shape.*—Ovate.

*Average length.*—2.25 cm.

*Average width.*—1.25 cm.

*Apex.*—Acuminate.

*Base.*—Cuneate.

*Margin.*—Entire to slightly crenate.

*Texture of top surface.*—Leathery. Very slight pubescence in Spring.

*Texture of bottom surface.*—Leathery. Very slight pubescence in Spring.

*Color.*—Young foliage upper side: Spring: Greyed-Yellow 160A. Summer: Greyed-Orange N163D to Yellow-Green 152B. Fall: Greyed-Red 179B. Young foliage under side: Spring: Greyed-Orange N167D. Summer: Greyed-Orange 167C to near Grey-Brown 199B. Mature foliage upper side: Spring: Yellow Green 144A. Summer: Varying amounts of Yellow-Green 150D and Green 143A. Fall: Greyed-Red 179B, flushed 180A and 183C. Mature foliage under side: Spring: Yellow Green 144C. Summer: Varying amounts of Yellow-Green 150D and Green 143C. Fall: Greyed-Red 179B, flushed 180A.

*Venation.*—Pattern: Pinnate. Color upper side: Spring: Near Yellow-Green 144A. Summer: Indistinguishable from leaf blade. Fall: Greyed-Red 178A. Color under side: Spring: Near Yellow-Green 144C. Summer: Near Yellow-Green 144C. Fall: Greyed-Red 178C.

*Petiole.*—Average Length: 2 mm. Diameter: 1 mm. Petiole color upper side: Near RHS Yellow-Green 144A. Petiole color lower side: Near RHS Yellow-Green 145C. Petiole Texture upper side: Smooth. Petiole Texture lower side: Smooth.

FLOWER

Natural flowering season: Summer to Fall.

Flowering form: Single funnelform flowers clustered on flowering stem ends.

Quantity of flowers per flowering stem/inflorescence: About 10.

Inflorescence width: 5-8 cm.

Inflorescence height: 7-19 cm.

Flower aspect: Somewhat downward facing.

Size:
*Length.*—1.75 cm.
*Diameter.*—1.75 cm.
Flower other characteristics:
*Persistence.*—Self-cleaning.
*Fragrance.*—Light and sweet.
*Longevity.*—About 7-10 days.
Bud:
*Shape.*—Round.
*Length.*—1.0 cm.
*Diameter.*—5 mm.
*Color.*—Greyed-Purple 186D.
Petal:
*Petal arrangement.*—Single funnelform.
*Number of petals per flower.*—5.
*Petal shape.*—Elliptic-Obovate.
*Petal base.*—Fused.
*Margin.*—Entire.
*Tip shape.*—Obtuse.
*Unfused length.*—5 mm.
*Unfused width.*—5 mm.
*Tube length.*—About 1.3 cm.
*Tube width.*—Widest point about 7 mm, narrowest point about 4 mm.
*Texture.*—Inner: Pubescent. Outer: Smooth.
*Appearance.*—Delicate, with slightly matte appearance upper and lower surfaces.
Color:
*When opening.*—Inner surface: Near Purple 76B. Throat 76D. Outer surface: Near Purple 76A, throat 76D.
*Fully opened.*—Inner surface: Near Purple 76C. Throat White N155B. Outer surface: Near Purple 76D, throat White N155C.
*Fading to.*—Inner surface: Near Purple 76D. Throat White N155B. Outer surface: Near Purple 76D, throat White N155C.
Sepal:
*Arrangement.*—Whorl.
*Number.*—Average 5.
*Shape.*—Linear to oblanceolate.
*Tip.*—Acute.
*Base.*—Cuneate.
*Margin.*—Entire.
*Length.*—7.5 mm.
*Width.*—5 mm.
*Texture, upper.*—Glabrous.
*Texture, lower.*—Glabrous.
*Color.*—Mature: Inner surface: Edges Red 39B fading to yellow orange 20C in center. When flower falls off, turns yellow 13D and remains on plant. Outer surface: Edges Red 39B fading to yellow orange 20C in center.
Peduncle:
*Length.*—5 mm.
*Diameter.*—2 mm.
*Color.*—Near Red 39B.
*Orientation.*—About 45°, or less.
*Strength.*—Good.
*Texture.*—Smooth.
Pedicel:
*Length.*—5-7 mm.
*Diameter.*—1 mm.
*Strength.*—Moderate.
*Texture.*—Glabrous.
*Color.*—Red 39B.

REPRODUCTIVE ORGANS

Stamens:
*Number.*—Average 4.
*Filament length.*—1.0 cm.
*Filament color.*—Near RHS White N155D.
Anthers:
*Shape.*—Narrow elliptic.
*Length.*—2 mm.
*Color.*—Near RHS White N155D.
*Pollen color.*—Near RHS White N155D.
*Pollen amount.*—Moderate.
Pistil:
*Number.*—1.
*Length.*—1.0 cm.
*Style.*—Length: 1.0 cm. Color: Near RHS White N155D.
*Stigma.*—Shape: Orbicular. Color: Near RHS White N155D.
*Ovary color.*—Near Yellow-green; 150D.

OTHER CHARACTERISTICS

Seeds and fruits: Not observed.
Disease/pest resistance: Neither resistance nor susceptibility to normal diseases and pests of *Abelia grandiflora* have been observed.
Temperature tolerance: Typical range USDA zones 5 through 9.
What is claimed is:
1. A new and distinct cultivar of *Abelia* plant named 'MINACARA1' as herein illustrated and described.

* * * * *